United States Patent
Batch

(10) Patent No.: US 10,387,619 B2
(45) Date of Patent: *Aug. 20, 2019

(54) MEDICATION ORDER PROCESSING AND RECONCILIATION

(71) Applicant: CAREFUSION 303, INC., San Diego, CA (US)

(72) Inventor: Richard M. Batch, Del Mar, CA (US)

(73) Assignee: CareFusion 303, Inc., San Diego, CA (US)

(*) Notice: Subject to any disclaimer, the term of this patent is extended or adjusted under 35 U.S.C. 154(b) by 241 days.

This patent is subject to a terminal disclaimer.

(21) Appl. No.: 14/195,750

(22) Filed: Mar. 3, 2014

(65) Prior Publication Data

US 2014/0180716 A1 Jun. 26, 2014

Related U.S. Application Data

(63) Continuation of application No. 11/325,782, filed on Dec. 30, 2005, now Pat. No. 8,666,760.

(51) Int. Cl.
*G06F 19/00* (2018.01)
*G06Q 50/22* (2018.01)

(52) U.S. Cl.
CPC ......... *G06F 19/3456* (2013.01); *G06Q 50/22* (2013.01); *G06F 19/325* (2013.01)

(58) Field of Classification Search
CPC .. G06F 19/3462; G06F 19/322; G06F 19/324; G06Q 50/24; G06Q 10/1097;
(Continued)

(56) References Cited

U.S. PATENT DOCUMENTS 3,913,118 A * 10/1975 Abrams ................. B42D 15/00
281/2
5,616,899 A * 4/1997 Recigno ................. G16H 10/40
235/375

(Continued)

FOREIGN PATENT DOCUMENTS

JP 2004078629 A 3/2004
JP 2006501874 A 1/2006
(Continued)

OTHER PUBLICATIONS

Communication pursuant to Article 94(3) EPC for European Application No. 06845794, dated Feb. 12, 2009, 6 pages.
(Continued)

*Primary Examiner* — Reinald R Reyes
(74) *Attorney, Agent, or Firm* — Morgan, Lewis & Bockius LLP

(57) ABSTRACT

A system and method for managing medication orders, including verbal orders and changes to those orders, is described. A server receives mediation orders from a pharmacy and communicates those orders to an infusion pump. The infusion pump communicates status messages to the server and the server compares the status messages to the medication orders to determine if the there were any changes to the order, or if a medication was administered absent a medication order. The server assigns a new order identification number to the status message if needed. The system may also reconcile original medication orders with information associated with a new order identification number and stores the information in the eMAR of a patient.

20 Claims, 4 Drawing Sheets

(58) Field of Classification Search
CPC ........ A61K 38/00; A61B 5/0002; A61B 5/02; A61B 5/14532
See application file for complete search history.

(56) References Cited

U.S. PATENT DOCUMENTS

| | | | | |
|---|---|---|---|---|
| 5,771,657 | A * | 6/1998 | Lasher | B65B 5/103 53/55 |
| 5,911,687 | A * | 6/1999 | Sato | G06F 19/324 600/300 |
| 6,249,282 | B1 * | 6/2001 | Sutcliffe | G06Q 30/02 707/999.006 |
| 6,311,211 | B1 * | 10/2001 | Shaw | G06Q 10/107 709/206 |
| 6,330,491 | B1 * | 12/2001 | Lion | G06F 19/3462 700/237 |
| 6,551,243 | B2 * | 4/2003 | Bocionek | A61B 5/411 600/300 |
| 6,711,463 | B2 * | 3/2004 | Tozuka | B64F 1/366 700/225 |
| 6,771,369 | B2 * | 8/2004 | Rzasa | G01J 3/02 356/326 |
| 7,343,224 | B2 * | 3/2008 | DiGianfilippo | A61K 9/0019 700/265 |
| 2002/0165736 | A1 * | 11/2002 | Tolle | G06F 19/328 705/3 |
| 2003/0135388 | A1 * | 7/2003 | Martucci | A61M 5/142 705/2 |
| 2003/0140928 | A1 | 7/2003 | Bui et al. | |
| 2004/0176984 | A1 | 9/2004 | White et al. | |
| 2005/0125097 | A1 * | 6/2005 | Chudy | G06F 19/3462 700/236 |
| 2005/0224083 | A1 * | 10/2005 | Crass | G06F 19/326 128/897 |
| 2008/0219405 | A1 * | 9/2008 | Falco | A61N 5/1049 378/65 |

FOREIGN PATENT DOCUMENTS

| | | |
|---|---|---|
| JP | 2007525256 A | 9/2007 |
| WO | WO-2003063932 A2 | 8/2003 |
| WO | WO-2005055112 A2 | 6/2005 |
| WO | WO-2005060673 A2 | 7/2005 |
| WO | WO-2005101279 A2 | 10/2005 |

OTHER PUBLICATIONS

Communication pursuant to Article 94(3) EPC for European Application No. 06845794, dated Oct. 1, 2012, 7 pages.
English Translation of Japanese Office Action for Japanese Application No. 2008-548607, dated Jul. 13, 2012, 2 pages.
English Translation of Japanese Office Action for Japanese Application No. 2008-548607, dated Nov. 10, 2011, 2 pages.
International Preliminary Report on Patentability for International Application No. PCT/US2006/048393, dated Jul. 10, 2008.
International Search Report for International Application No. PCT/US2006/048393, dated Aug. 14, 2007.
New Zealand Office Action for New Zealand Application No. 569955, dated Dec. 9, 2009, 2 pages.

* cited by examiner

MEDICATION ORDER PROCESSING AND RECONCILIATION

CROSS-REFERENCE TO RELATED APPLICATIONS

The present application is a continuation application of and claims priority to U.S. patent application Ser. No. 11/325,782 entitled "MEDICATION ORDER PROCESSING AND RECONCILIATION," filed on Dec. 30, 2005, U.S. Pat. No. 8,666,760, the entire contents of which are incorporated by reference herein for all purposes.

BACKGROUND OF THE INVENTION

This invention relates generally to automated hospital information systems and systems for providing, monitoring and automating the administration of medication to patients in those institutions, and in particular to a system and method for reliably and accurately tracking medication administration events and reconciling those events with medications orders issued by an institutions pharmacy.

Medication delivery in a hospital or care giving institution is a daunting task that has proven to be difficult to automate. One reason for this is that there are many instances in such an institution where medication is given, or the way the medication is given, is changed without having a written or electronic order. Even where there is an order in place, changes to the delivery mode, even where recorded, may not be reconciled to the original order.

Typically, the administration of medication in an institution begins with a physician or other authorized care giver creating a medication order. The order is then communicated to the institution's pharmacy, either in written form, or in electronic form. The pharmacy prepares the medication according to the order, generally assigning a unique identifier to the medication order, such as a number. The intent of such a system is to be able to track the order through the pharmacy and ultimately to the patient using the unique order number.

Once the medication is prepared by the pharmacy, it is usually labeled with information pertinent to the delivery of the medication. For example, in the case of a medication that is to be delivered by infusion, a bag of infusion fluid containing a prescribed medication is labeled with information such as the medication order number, patient information, such as a name or other identification means, and perhaps information related to the delivery of the infusion fluid, such as rate of infusion or volume to be infused.

The medication is then transferred to the location of the patient, where it is administered. In the case of a medication to be administered via infusion, the fluid containing infusion bag is hung at the patient's bedside, and an infusion pump is used to administer the fluid in a controlled manner to the patient.

In some cases, one or more of the parameters used to program the delivery of fluid to the patient are adjusted during infusion of the medication, such as when monitoring of the patient's vital signs indicates that the rate of delivery needs to be increased or decreased to obtain a desired result. This process is call titration. In prior art systems, such adjustments were not automatically recorded to a patient's medication administration record, but instead needed to be manually entered by a care giver.

In other instances, oral orders are issued and medication delivery begun before receiving a medication order from the pharmacy. Again, in many prior art systems, there was no way to automatically record and track this medication delivery, because there was no pharmacy generated order, and the only way to ensure that the patient's medication record was complete is to manually enter the information and then reconcile the manually entered record with a post delivery generated medication order. Similarly, at times, the nurse or care giver may use floor stock to replenish a medication. Such floor stock typically carries no patient identification information because it was not dispensed by the pharmacy for delivery to a particular patient. While every effort is made to insure the integrity of a patient's medication record, such manual entry and reconciliation provide opportunities for errors in the record, errors which could be avoided in a system that was capable of assigning an order identification number that could then be automatically reconciled with pharmacy generated medication order numbers and recorded into a patient's medication administration record.

Accordingly, what has been needed, but heretofore unavailable, is a system capable of recognizing actions that occur during medication delivery to a patient that could be due to a new order, and which is able to determine if a new order number should be applied to the medication delivery. The system would generate order identification numbers for each action determined to require a new order number. Such a system would be particularly useful when used in conjunction with an infusion system to capture orally ordered medication starts and medication titrations, either where the titration is performed for effect or because a new prescription is issued, to ensure a complete electronic medication administration record. The present invention satisfies these and other needs.

SUMMARY OF THE INVENTION

In a general aspect, the system and method of the present invention is embodied in a system that track medication being given to a patient, determines whether an event has occurred during administration of the medication that requires a new order identification number, assigns the new order identification system if necessary, reconciles the new order identification number with existing order information, if any, and updates an electronic medication administration record for the patient with the reconciled information.

In another aspect, the present invention is embodied in a system for managing medication orders, comprising a server configured to receive a medication order containing medication administration information from a medication order source, a medication administration device in operable communication with the server, the medication administration device capable of receiving medication administration information from the server, and also capable of providing the server with medication administration status information, wherein the server compares medication administration status information received from the medication administration device to the medication administration information in the medication order, and if the server determines that there are differences between the medication administration status information and the medication administration information of the medication order, the server associates a new order identification number to the medication administration status information. In another aspect, the medication order includes a medication order number, and in still another aspect, the server associates the new order identification number with the medication order number.

In a further aspect, the invention includes a medication administration record database in operable communication with the server, and in yet a further aspect, the server communicates medication administration status information, including medication administration status information associated with the new order identification number, to the medication administration record database for storage in that database.

In still another aspect, the invention comprises a medication administration record database in operable communication with the server, and wherein the medication status information includes the medication order number and the server communicates the medication administration status information, including medication administration status information associated with the new order identification number, to the medication administration record database for storage in that database. In yet another aspect, the invention includes a processor in communication with medication administration record database, the processor configured to reconcile medication administration status information including the new order identification number with medication order to provide a complete record of medication administration to a patient.

In yet another aspect, the invention is embodied in a method for managing medication orders used to identify delivery of medication to a patient, comprising associating a medication order number to a medication order, the medication order including medication administration information, communicating the medication order number to a processor in communication with a medication administration device, communicating the medication administration information from the processor to the medication administration device, communicating medication administration status information from the medication administration device to the processor, comparing the medication administration status information to the medication administration information of the medication administration order, and associating a new order identification number with the medication administration status information if the comparison indicates a difference between the medication administration information and the medication administration status information. In a further aspect, the invention includes communicating the medication administration status information including the new order identification number to a medication administration record database, and storing the medication administration status information including the new order identification number in the medication administration record database. In a still further aspect, storing includes storing the medication administration status information including the new order identification number in an electronic medication administration record of a patient, and in yet another aspect, the method includes reconciling the medication administration status information including the new order identification number stored in the medication administration record database with the medication order.

In still another aspect, comparing includes applying one or more rules selected from a database of rules to the communicated medication administration status information to determine if a new order identification number is applied to the communicated medication administration status information. In yet another aspect, the database of rules contains at least one institutionally determined rule.

In a still further aspect, the present invention is embodied in a method for ensuring that medication delivery changes are captured and communicated to an electronic medication administration record, comprising monitoring medication delivery change actions, flagging medication delivery change actions, determining whether a flagged medication delivery change action is a new medication delivery order, assigning a new order identification number to the flagged medication delivery change action if it is determined that the flagged change action is a new medication delivery order, reconciling the new order identification number with an original order number into electronic medication record administration data, and updating an electronic medication administration record with the electronic medication record administration data.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

Figure 1:
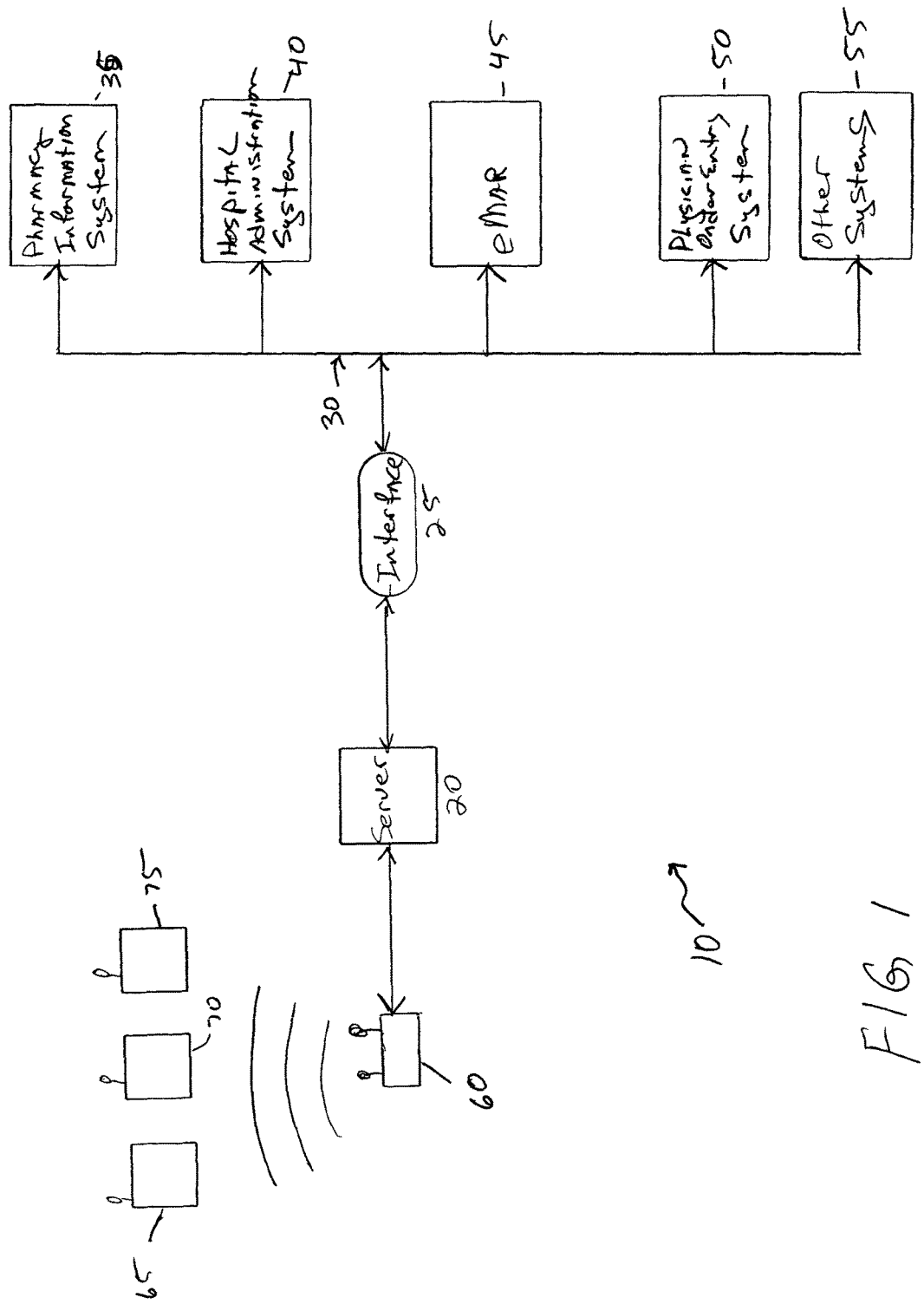
FIG. 1 is a schematic block diagram of an institutional information system providing for communication of patient and medication related information among various institution subsystems and medical devices for administering medication and monitoring patient vital signs.

Referring now to the drawings in detail, in which like reference numerals indicate like or corresponding elements among the several figures, there is shown in FIG. 1 generally an integrated hospital-wide information and care management system 10. The care management system embodiment shown in FIG. 1 is depicted as being a configured as a local area network with a server 20 to which is connected, through an interface 25, various hospital information and administration systems 35, 40, 45 50 and 55, as well as medical devices 65, 70, 75, which may be medication administration devices, monitoring devices, bar code readers and the like. In the embodiment shown, medical devices 65, 70 and 75 communicate with server 20 via a wireless communication system utilizing a wireless access point 60.

While the system described above is described as a local area network, other network configurations are possible. For example, the network may be configured as a wide area network, or the network may be configured including remote computers and databases, or may utilize the internet or other communication means to provide for remote control and data flow within the network.

Referring again to FIG. 1, the server 20 stores programs and data collected by the various computers and systems in the local area network. Various application modules of the patient management system may be resident in each of the computers in the network and will be discussed in more detail below. Ethernet cabling of a local area network 30 is used to connect various computers and information systems to the server 20. The server 20 may also have both local and network hard disk storage for storing programs as well as data gathered on the network.

As shown in FIG. 1, various subsystems of a facility's information management system are connected together by way of the communication system 30. The communication system 30 may be, for example, a local area network (LAN), a wide area network (WAN), Internet- or Intranet-based, or some other telecommunications network designed to carry signals allowing communications between the various information systems in the facility. For example, as shown in FIG. 1, the communication system 30 connects, through various one or more interfaces 20 (only one shown), a pharmacy information system 35, a hospital administration system 40, a an electronic medication administration record systems 45, physician order entry system 50, and other systems 55, which may be, for example, a laboratory data system, a paging system, an alerts management system, a report generating system, and the like.

Each of the various systems 20, 35, 40, 45, 50 and 55 are typically interconnected via the network 30 and appropriate interfaces 20, and generally comprise a combination of hardware such as digital computers which may include one or more central processing units, high speed instruction and data storage, on-line mass storage of operating software and short term storage of data, off-line long-term storage of data, such as removable disk drive platters, CD ROMs, or magnetic tape, and a variety of communication ports for connecting to modems, local or wide area networks, such as the network 30, and printers for generating reports. Such systems may also include remote terminals including video displays and keyboards, touch screens, printers and interfaces to a variety of clinical devices. The processors or CPUs of the various systems are typically controlled by a computer program or programs for carrying out various aspects of the present invention, as will be discussed more fully below, and basic operational software, such as a Windows™ operating system, such as Windows NT™, Windows 2000™, or Windows XP™, distributed by Microsoft, Inc., or another operating program distributed, for example, by Linux, Red Hat, or any other suitable operating system. The operational software will also include various auxiliary programs enabling communications with other hardware or networks, data input and output and report generation and printing, among other functions.

The communication system 30 may comprise, for example, an Ethernet (IEEE 522.3), a token ring network, or other suitable network topology, utilizing either wire or optical telecommunication cabling. In an alternative embodiment, the communication system 30 may comprise a wireless system, utilizing transmitters and receivers positioned throughout the care-giving facility and/or attached to various computers, clinical devices and other equipment used in the facility. In such a wireless system, the signals transmitted and received by the system could be radio frequency (RF), infrared (IR), or other means capable of carrying information in a wireless manner between devices having appropriate transmitters or receivers may be used. It will be immediately understood by those skilled in the art that such a system may be identical to the system set forth in FIG. 1, with the exception that no wires are required to interconnect the various aspects of the system.

In the embodiment shown, the server 20 of the care management system is connected by the local area network (LAN) 30 to computers and other peripheral equipment located in the institution's pharmacy, at nursing stations located throughout the institution, and at the patient's bedside. In one embodiment, the module located in the pharmacy may comprise a central processing unit to which is attached a video display and a keyboard for entry and display of patient information and drug parameters. Also attached to the pharmacy CPU is a bar code reader which is adapted to read barcode labels that may be attached to drug containers, equipment, or caregiver identification badges. Also connected to the pharmacy CPU may be a bar code printer and a printer used for generating reports containing information about patient history and/or patient treatment. The printer may also be used to print barcode labels generated by the pharmacy CPU after patient or drug data is input by a technician or pharmacist into the pharmacy computer using the keyboard or other means. In accordance with one embodiment of the present invention, the pharmacy CPU is located at a central pharmacy that serves an entire healthcare facility or a particular section or unit of the facility. As will be discussed in more detail below, with the use of the pharmacy CPU, a pharmacist can monitor all medication orders for the facility or specified unit, as well as the progress of those orders, and manage the administration of medication to ensure that the medication is administered to the right patient, in the right dose, along the right route and at the right time.

In some embodiments, the system may also include another computer, located at a nursing station. Nursing stations are typically located in various sections and/or floors of a hospital or clinic and generally provide a central location for record storage and monitoring for a number of patient beds. The nursing computer or CPU located at the nurse station typically includes a video display for displaying patient or other information pertaining to the operation of the particular unit of the institution, and a keyboard, mouse, touch screen, or other means for entering patient data or specific commands instructing the nursing CPU to generate reports relating to either the patient's medical history or the course and progress of treatment for an individual patient on the attached printer or on the video display. The nursing station CPU may also generate other reports such as, for example, a printout of drugs scheduled to be administered to patients, productivity measurements such as, for example, the amount of time a nurse spends with a patient or other reports useful for assisting in the efficient operation of the particular unit or the hospital. For example, a report listing the actual times of administration versus the scheduled times for administration may be prepared to assist in evaluation of staffing requirements.

Each care unit associated with the nursing station typically comprises one or more patient beds located in private rooms, shared rooms, or open or semi-open wards that contain multiple beds. In accordance with an embodiment of the present invention, each private room, semi-private room, or ward area has at least one medical device for delivering medication and/or monitoring the status of a patient located therein. The medical device may have a central controller or CPU for controlling medication administration and for gathering dated related to medication administration and patient status. Moreover, each patient bed or group of beds may also have a bedside computer or CPU for monitoring and controlling one or more medical devices for treating patients. In systems having bedside computers, the bedside CPU may include a video display and a keyboard, mouse, touch screen or other device. The bedside CPU can be used by a nurse, physician or technician to access a variety of institutional databases to display a variety of information about a particular patient. This information can include an on-line, real-time, graphical patient medication administration record (eMAR) that is maintained separately from other systems or that is derived from the patient's medication profile maintained by another system in the hospital, such as by the hospital's pharmacy information system 35, the hospital information system 40 or other systems.

The bedside CPU also allows remote access to a patient's records stored by the server 20 to display medication history for the patient. This medication history includes a listing of all drug or other treatments given to the patient, including past, present and future deliveries of medications to the patient. While a bedside CPU has been described, it will be understood that what is intended is a system having a computer or processor located in the general vicinity of a patient. Such a computer or processor, besides being embodied in a bedside computer, may also be incorporated in a handheld or vital signs device, a laptop computer, a personal digital assistant (PDA), a controller for an infusion pump, or any other suitable device having a processor capable of being programmed to carry out the functions described above.

In one embodiment of the present invention, the bedside CPU further includes a database including a library or libraries of information concerning past and present medical administration activities and/or institutional guidelines for appropriate parameters for administration of various medications. For example, the guidelines may include institutionally established guidelines or limits on drug administration parameters, such as dosage, frequency of administration, and other delivery related information such as, for example, appropriate flow rates and infusion durations for programming infusion pumps. Additionally, the guidelines may encompass guidelines or rules for providing drug administration appropriate to particular patient treatment areas having different sets of delivery parameters for similar medications, such as medication administration directed to geriatric, pediatric and oncology patients. Guidelines may also be included that are directed to particular therapy regimens, such as chemotherapy regimens or regimens for treating chronic infection or pain. The guidelines library stored in the bedside CPUs may be accessible by the medication administration devices during programming of an infusion. Alternatively, the database may be stored directly in the medication administration device or another computer connected to the network and accessible by the medication administration device. In one embodiment, the database may be stored in the server 20 or the pharmacy information system 35 and accessed and controlled by the central pharmacy to supervise medication administrations delivered by the medication administration device. In another embodiment, the database may be stored in a mobile device, such as a notebook computer, PDA, computer on wheels, or the like.

Each bedside CPU, or medical device including a suitably programmed processor, computer or controller, can be connected through an appropriate interface to a variety of peripheral equipment. For example, the system may include a barcode reader capable of reading barcodes on a patient's wristband or medication container; an infusion pump for delivering medication to the patient in a predetermined, controlled manner; or various sensors that can automatically monitor a patient's vital signs and send signals representative of these vital signs to the computer through an appropriate interface for storage and later retrieval by a selected software application to provide a graphic display of the patient's vital signs during the course of treatment.

In a different embodiment where RFID (RF identification) tags may be used with medication, patients, equipment, or in other ways, the bedside CPU may also include an interrogator or RFID reader (not shown) for use with the RFID tags.

Figure 2:
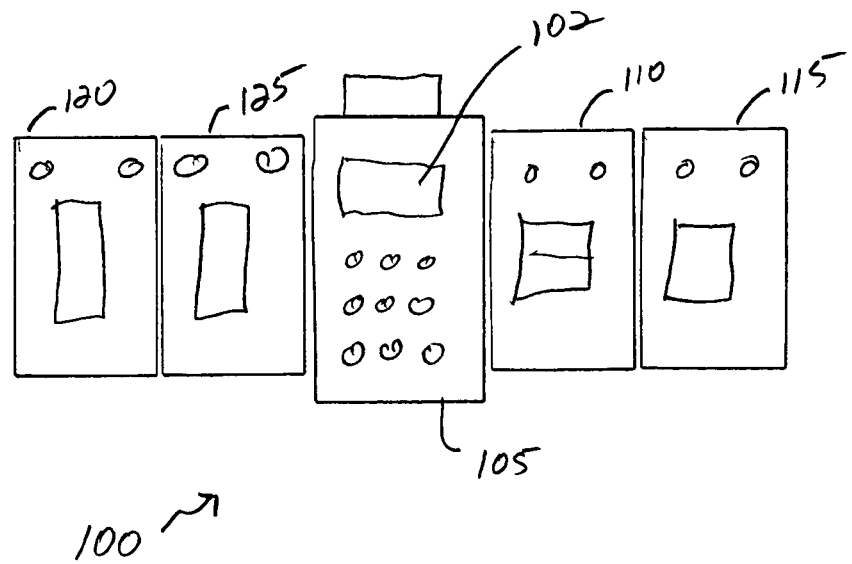
FIG. 2 is a graphical representation of a medication administration device having a central controller and various modules for delivering medication, monitoring patient vital signs, and for receiving identification data related to patients, care givers and medications.

FIG. 2 illustrates one embodiment of a bedside medication administration device 100 capable of controlling and monitoring one or more medication delivery devices, vital signs monitors and/or identification modules. In the system depicted in FIG. 2, four different functional units are shown mounted on and in operable communication with a central controller 105. Central controller 105 includes a processor, memory and a communications port for providing a communication pathway to and from the hospital's network 30 (FIG. 1).

Functional units shown include an infusion pump unit 110, a syringe pump 115, a pulse oximeter 120, and a bar code reader 125. In one embodiment, it would be possible to select a functional unit to perform a particular function or procedure through controller 105 by depressing an appropriate softkey or hardkey programmed to associate a functional unit with the display of the central controller 105. When the desired functional unit is selected, display 102 of the controller 105 is configured so as to act as the user interface for the selected functional unit. More specifically, display 102 is configured in accordance with a function specific domain to provide function specific displays and softkeys which may be operated to program and operate the functional unit.

Infusion pump unit 110 shown in FIG. 2 is a pumping unit for basic fluid infusion. Infusion pump unit 110 includes a system to control the various functions performed by such a pump, which include the control of fluid delivery to the patient and the monitoring of the fluid path for occlusion or air-in-line. Infusion pump unit 110 may contains one or more displays, such as a rate display used to display the actual infusion rate at which the pump is operating and a channel message display used to display informational, advisory, alarm, or malfunction messages. Infusion pump unit 110 may also contains a plurality of indicators, which illustratively illuminate when the functional unit is in alarm or infusion complete condition, when the functional unit is programmed for a future start time or has been paused, or when the functional unit is performing an infusion. Other appropriate indicators may be included in other functional units.

Also shown in FIG. 2 is syringe pump 115, a pulse oximeter 120 and a bar code reader module 125. Syringe pump 115, pulse oximeter 120 and the bar code reader module 125 may each contain a set of hardkeys and/or softkeys for operating the functional unit. Each of the functional units may also include one or more displays and a plurality of indicators which may be used to display appropriate information.

With the advent of computers and networking capabilities, hospitals and other care giving institutions have developed or purchased various systems for recording and tracking the treatment given to patients. One method commonly used is the recording and maintaining of an electronic medication administration record, typically called an eMAR, that contains details of each medication administration given to a patient in the institution. The eMAR is a document that, to be useful, must be accurate, and contain a complete record of a patient's treatment.

A patient entering a hospital or other care giving facility is provided with a wristband, necklace, ankle band or other identifier that is affixed to the patient in a manner so that the patient can be identified even if the patient is unconscious or otherwise unresponsive. This wristband or other device may include a bar code representing the name of the patient and other information that the institution has determined is important. Additionally, any other information such as age, allergies, or other vital information may be encoded into the bar code. Alternatively, the patient information device may be an active embedded computer or passive device attached to a wrist band or other carrier that is attached to the patient. Such a device would be responsive to devices located throughout the care-giving facility, such as readers or wireless transmitter/receivers, to provide the identity of the patient along with other information when the device is queried.

After the patient is admitted and situated in a bed within the facility, the patient is typically evaluated by a physician and a course of treatment is prescribed. The physician prescribes a course of treatment by preparing an order which may request a series of laboratory tests or administration of a particular medication to the patient. In some case, the physician prepares the order by filling in a form or writing the order on a slip of paper to be entered into the hospital system for providing care. In other cases, the physician may enter the medication order directly into a physician order entry system 50 (FIG. 1) or may instruct a nurse or other care-giving professional to do so.

If the order is for administration of a particular medication regimen, the order will be transmitted to the facility's pharmacy information system 35. Using the pharmacy CPU, the pharmacy reviews the order. The pharmacy information system 35 typically checks each order against a database of medication related information for incompatibilities, including interactions with other drugs and with patient conditions, such as patient allergies, diseases, and vital signs. If no incompatibilities are detected, the pharmacy prepares the medication according to the requirements of the physician. Typically, the pharmacy packages the medication in a container, and a copy of the order, or at a minimum the patient's name, the drug name, and the appropriate treatment parameters, including a medication order identification number, are represented on a label that is affixed to the drug container. This information may be represented by a bar code, or it may be stored in a smart label, such as a label having an embedded computer or passive device.

Once the order has been prepared, the order is sent to the nurse station for matching with the appropriate patient. Alternatively, if the medication is for a commonly or routinely prescribed medication, the medication may be included in an inventory of medications that is stored in a secure cabinet adjacent the nurse station. In such a case, the nurse station will receive from the pharmacy a list of the orders stored in the pharmacy information system 35 that may be drawn from the inventory adjacent the nurse station. The nurse enters her identifier at the cabinet to gain access, in accordance with standard practice. The nurse or other professional assigned the task of gathering medications then matches the orders received from the pharmacy information system 35 to the medications stored in the inventory and pulls those medications that are to be delivered to specific patients. These procedures are carried out whether the medication to be delivered is an oral medication, or a medication that is to be delivered intramuscularly or through an infusion.

When the prescribed time for delivery of the medications arrives, the medications are carried to the patient's area and administered to the patient by the nurse or other care-giver. In the case of drugs to be delivered via infusion, the care-giver hangs the infusion bag, attaches the bag to an infusion pump, and sets up the infusion pump to deliver the medication by programming the pump with values for various parameters that are used by the pump to control delivery of the medication to the patient.

For certain drugs, the care-giver is prompted to enter data descriptive of a selected patient parameter or parameters, such a laboratory value or a current vital sign, before completing the verification process. For example, the care-giver may be prompted to measure and enter a value for a patient's blood pressure before administering certain selected drugs. The system may include ranges of acceptable values for the parameters. If the system detects an out-of-range value for the parameter, the system causes an alarm to be provided. In an alternative embodiment, the parameters could be monitored and entered into the system automatically, eliminating the need for manual entry by the care-giver.

Once the medication delivery parameters and any other data is entered into the pump, the data is communicated to server 20 (FIG. 1) which in turn may communicate the information to the pharmacy information system 35, hospital administration system 40, eMAR system 45 or other system for recordation, monitoring and/or analysis. Typically, the information is communicated by the server over network 30 to the eMAR system 45 which records the therapeutic regimen information in the patient's eMAR, and verifies that the right medication is being given to the right patient in the right dose by the right route and at the right time.

In an embodiment of the present invention, where the medication is to be delivered using an infusion pump, such as the infusion pump 110 attached to the central controller 105 (FIG. 2), the care management system may be programmed to automatically download information consisting of the appropriate configuration parameters for the infusion from the pharmacy CPU through the network 30, server 20 and wireless access point 60. The signals transmitted from the wireless access point 60 are received by medical devices 65, 70 and 75, which may be a controller/pump system such as that shown in FIG. 2. Such configuration parameters are downloaded into the pump 110 to program the operation of the pump when the verification function that is carried out either in the processor of the central controller 105, the server 20, or in some other hospital information system is complete. This is particularly advantageous in that one potential source of inaccuracy is eliminated by automatically configuring the pump, thus eliminating the need for the nurse or technician to manually enter the parameters necessary to configure the infusion pump. In an embodiment where the pump cannot be automatically configured by downloading parameters from the network, the care management system only verifies that the right treatment is being administered to the right patient. The pump must then be manually configured by the physician, nurse or technician.

In one embodiment of the present invention, institutional guidelines for appropriate parameters associated with the entered parameters such as maximum and minimum doses may be stored in the database along with the guidelines relating to drug and patient condition incompatibilities. The pump, or other medication administration device, may also have a database of guidelines for appropriate parameters associated with the entered parameters stored within a memory associated with the pump or medication administration device. In the case where patient care systems or medication administration devices are connected to a hospital server, such a database may also be located at the hospital server and the patient care system or medication administration device communicates with the server during the verification stage to obtain the acceptable ranges. In another embodiment, the library may be located in a portable data assistant (herein "PDA") such as a Palm Pilot™ with which the patient care system or medication administration device may communicate via infrared link, RF, blue tooth, or by other means. The nurse or care-giver may carry the PDA and before the patient care system or medication administration device will begin operation, it must communicate with the PDA to compare the hard and soft limits against the entered values.

Once medication administration values have been entered into the patient care system or medication administration device by a nurse or other care-giver, these values are checked against the stored database to verify that the selected values are within acceptable ranges. If a selected value contravenes a hard limit, the processor will alarm and require a value change before operation of the medication administration device can begin. If the selected value contravenes a soft limit, the processor of the medication administration device will require an acknowledgment from the nurse or other care-giver that he or she understands the value entered is outside a soft limit and that this value is nevertheless to remain in force.

Storing a data base of institutional standards for drug infusion parameters and physiological parameter limits, such as, for example, the maximum and minimum concentrations of $CO_2$ and $SpO_2$ and the maximum and minimum values of respiration rate, also aids in standardizing the quality of care in a clinical setting. In some embodiments, infusion parameter values or physiological parameter limits may be entered automatically from a machine-readable label, for example using a bar code reader mounted on the bag or on the syringe or other medical fluid container in which the medical fluid to be infused is stored. In other embodiments, such infusion parameter values and physiological parameter values may also be entered by other means, such as through a connection with an external processor, such as a hospital server, through connection to a PDA, or other institutional systems. Connections with these devices may be made in various ways, such as direct, hardwired connection, infrared link, blue tooth link, or the like as know to those skilled in the art.

The medical database system of one embodiment of the present invention receives medication administration information from a nurse or care-giver prior to medication administration, compares that information to institutionally established guidelines for administration of various medications, and provides an alert if any or all of the medication administration information received from the medication administration device falls outside of the guidelines stored within the medical database. This allows the nurse or care-giver administering the medication to correct the administration parameters entered into the medication administration device before medication administration to the patient is begun. If the administration information falls within the guidelines, the nurse or care-giver may receive a message that medication administration may begin. In one embodiment, the medication administration device may be "locked out", that is, electronically prevented from beginning administration of the medication until the medication administration device receives a signal from the processor that the administration parameters entered into the administration device are appropriate for the medication and that institutional guidelines for the administration have been met, unlocking the medication administration device and allowing the care-giver to begin medication administration.

Once the infusion pump or other medication administration device is configured, the nurse, caregiver, or technician starts the infusion by pressing the appropriate control on the infusion pump 110. Starting a pump that is capable of being monitored automatically by the care management system causes a signal to be transmitted from the pump 110 through controller 105 to the wireless access point connected to server 20 (FIG. 1). Server 20 may then keep a record of the medication administration in its own memory or database, or may also communicate the relevant information to the hospital system, such as the eMAR system 45, for recordation in the patient's eMAR.

It will immediately be apparent to those skilled in the art that the medication order number is central to maintaining an accurate and complete record of medications delivered to a patients. All medication administrations are identified by a unique medication order identification number, which is then associated with a patient.

One problem that arises, however, is that changes may be made to an infusion regimen after the initial start of the infusion is recorded in the eMAR. However, these changes must also be recorded in the patient's eMAR to ensure a complete record of the medications given to the patient. Prior systems have not been capable of tracking these changes.

Moreover, in some situations, such as in the emergency room, or during an operation under anesthesia, oral orders are given for the administration of medications. In such cases, there is no pharmacy generated medication order identification number assigned, and so there is no way to ensure that the information is accurately communicated to and stored in the eMAR system.

Figure 3:
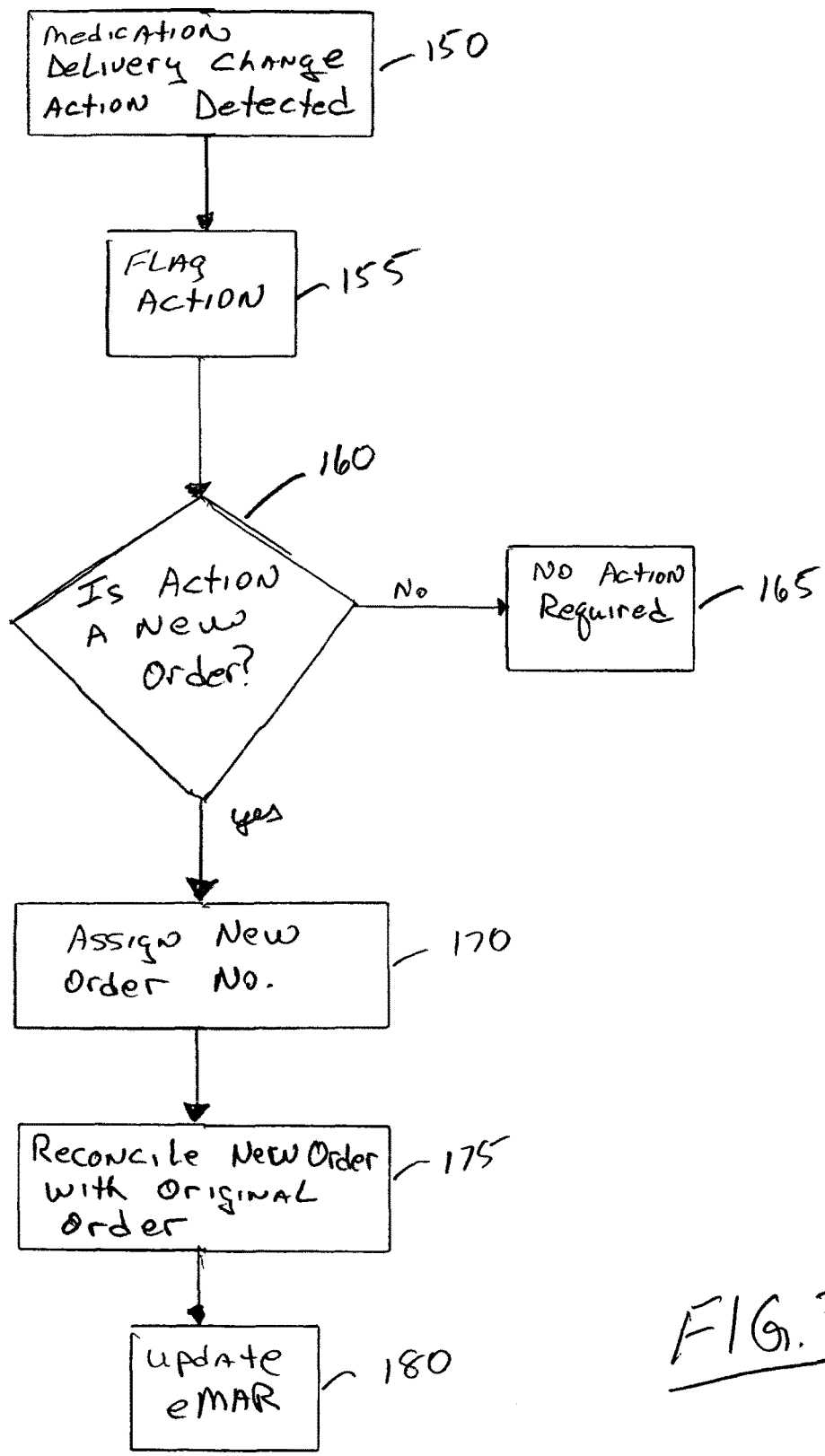
FIG. 3 is a block diagram of a process carried out ban embodiment of the present invention.

FIG. 3 contains a block diagram graphically illustrating a general embodiment of the system and method of the present invention. A medication delivery change action is detected by a medication delivery device, such as a suitably programmable infusion pump or central controller 105 (FIG. 2) in box 150. Medication delivery change actions may be actions such as the start up of the pump to deliver a new medication and the initiation of a medication delivery, the restart of the pump when a new bag is hung to replace a depleted bag of infusate, a change in the rate of medication delivery, a change in the amount of medication to be delivered, or other similar actions that may be required to be recorded to ensure a complete and accurate eMAR.

The pump flags the actions in box 155, identifying the action as one where a determination needs to be made as to whether a new order identification number should assigned to the action. The determination as to whether a new order identification number needs to be assigned to the flagged action occurs in box 160. A rules engine resident in the memory of the medication delivery device, or which is resident on a server, is then applied to the flagged action to determine the action is a new order that requires a new order identification number.

The rules engine, depending on where it is resident, may take different actions. For example, where the rules engine is resident on the pump, it may be programmed to take a conservative course of action and apply a new order number to each flagged action. If the rules engine is resident on a server, and acts on flagged actions communicated to the server by the pump, the rules engine may be more flexible, or may be programmed with institutional specific rules. Such institutional specific rules, for example, may include rules that determine that a flagged action does not require a new order identification.

If the rules engine determines that a flagged action is not a new order, the program branches to box 165, and no further action is taken, and medication delivery continues. If a flagged action is determined to be a new order, a new order identification number is assigned in box 170.

Medication administration information is then communicated to a server where the new order number is reconciled with the original order number associated with the medication delivery to ensure that the eMAR of the patient is complete and accurate. This reconciliation process may also be carried out in accordance with an institutionally developed set of rules which are applied to the various actions identified with order numbers to determine if the new order numbers should be considered as separate actions that require reconciliation with original order numbers. For example, in a system in accordance with one embodiment of the present invention, the program running on the server may deflag an action if it determines that the flagged action should not be accorded a new identification number. Such a system is particularly advantageous in that the pump can be programmed to flag each new action to ensure no change actions are missed, and the server can then determine, in accordance with institutional rules, whether each change actually needs a new identification number that will in turn need to be reconciled to an original order number. Once the reconciliation process is complete, the patient's eMAR is updated in box 180.

The specific activities carried out by the medication delivery device and server depend on the capabilities of the medication delivery device. For example, where the medication delivery device includes a suitably powerful processor, the new order identification number may be generated by the pump and the server accepts it for reconciliation. If the medication delivery device is not sufficiently intelligent, that is, does not include a suitably powerful processor, or lacks sufficient memory, and the like, the server may be configured to flag each action communicated to it and determine whether or not to assign a new identification order number.

Figure 4:
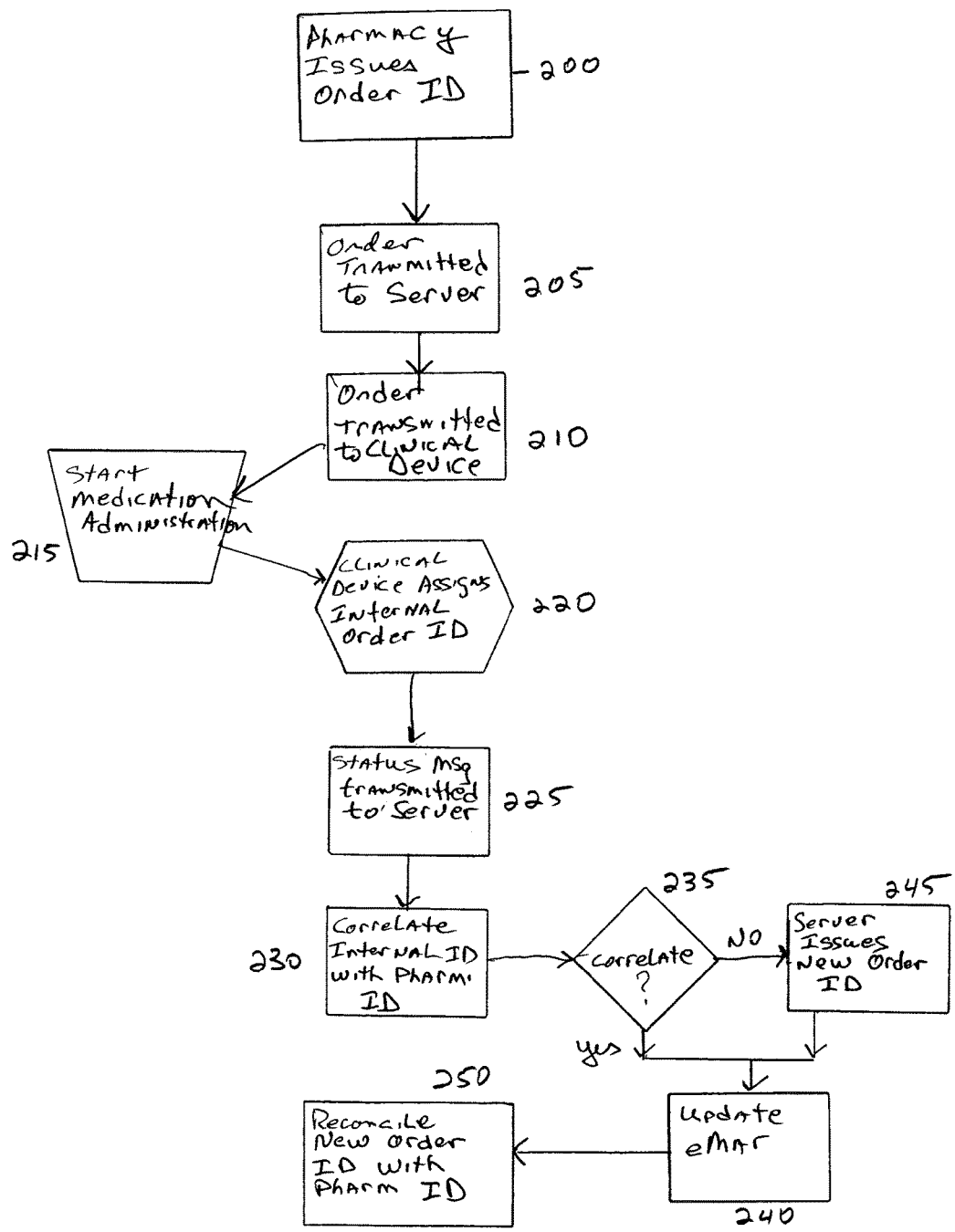
FIG. 4 is block diagram of a process carried out by another embodiment of the present invention incorporating principles of the embodiment of the present invention illustrated in FIG. 3.

A more detailed embodiment of a system and method in accordance with the present invention is illustrated by the flow chart of FIG. 4. As in normal practice, the pharmacy prepares a medication for delivery and issues an order identification number ("Pharm ID") in box 200. The Pharm ID, along with all of the other information necessary to administer the medication is then transmitted through the network 30 (FIG. 1) to the server 20 in box 205. In turn, the medication order is transmitted through the network to the appropriate medical device 65, 70, 75, which may be, for example, an infusion pump such as the Medley™ sold by Cardinal Health, for delivery to the patient in box 210.

As described previously, a medication administration device such as the Medley infusion system includes a central controller having a memory for storing computer programming and operational software and infusion and patient related data. The processor of the central controller can be programmed to both control the flow of programming commands into a functional module, such as an infusion pump, and also monitor the functional module for status information related to either the patient, the medication delivery, or both. The programming commands used to control the operation of the functional unit are typically received from server 20, which, as described, may receive them from another hospital system, such as the pharmacy information system 35. Alternatively, the central controller may receive programming commands directly from a hospital system.

At a predetermined time, a care giver will go to the patient's bedside to initiate delivery of an ordered medication. In the embodiment described, where the medication is to be given as an infusion, the care giver hangs the infusion bag containing the ordered infusate at the patient's bedside. At that time, depending on the system used by the hospital, the care giver may use an identification device, such as a bar code reader, to input the identification of the patient, the identification of the medication, and perhaps the identification of the care giver. If suitably programmed, the processor of the central controller of the medication administration device compares the patient's identification to that associated with the medication identification to ensure that the right medication is being given to the right patient. If this comparison is satisfied, then the server 20 may communicate various operating commands or configuration or operating parameters to the processor of the central controller to program the functional unit to deliver the medication as ordered. Alternatively, the operating commands or parameters may have already been communicated to the processor of the central controller, and a satisfied comparison of identification data allows the programming of the processor of the central controller to proceed to program the functional unit in accordance with those operating commands or parameters.

Additionally, the server 20 or the processor of the central controller may be programmed to carry out additional evaluation of the programming commands or operating parameters to be used to program the functional unit, particularly if one or more of the commands or parameters is entered or changed manually by the care giver. The commands and parameters may be compared by the processor to a library of guidelines and rules established by the hospital or institution. If the comparison indicates that the entry is outside of the established guideline or violates a rule, an alert may be provided, and the delivery of the medication halted or blocked until the entry is corrected.

Once all comparisons are completed and the processor of the central controller of the medication administration device determines that the right drug is being given to the right patient in the right form and dosage, and also at the right time, if the system is programmed to evaluate that parameter, the delivery of the medication may begin. While the system may be programmed to automatically start the infusion, typically the start of medication delivery is initiated by the care giver pressing a button, a key or actuating a mouse or some other means on the medication administration device or in communication with the medication administration device in box 215 (FIG. 3). In any case, once the medication delivery is actually started, the processor of the central controller assigns an internal order identification number (Internal ID) to the medication delivery in box 220. It will be understood that the Internal ID may be assigned to the medication order at any time once the medication order is received by the central controller; thus the scope of the invention is not limited to assigning an Internal ID only after initiation of medication delivery.

Depending on the programming of the central controller of the medication administration device 65, 70, 75 and the server 20 (FIG. 1), the central controller of the medication administration device may monitor the delivery of the medication and provide the server with periodic status messages containing information related to the delivery of the medication in box 225. These messages are coded with the Pharm ID and also the Internal ID, among other delivery related information. These messages may be provided to the server 20 by the central controller of the medication administration device either in an unsolicited manner, that is, they are sent to the server at predetermined intervals, or they may be solicited by the server. By this it is meant that the server 20, either automatically polls the medication administration device at selected intervals, or the server 20 polls the medication administration device upon request from a system user, to solicit a status message from the medication administration device.

Once the status message is received by the server 20, the server processes the information contained in the status message to determine what action should be taken next. For example, the server correlates the Pharm ID and Internal ID to determine if any action needs to take place. Alternatively, the server, in box 230, may perform such tasks as, for example, transposing status information as needed, matching information fields or identifications, cross referencing information as needed, forming new records from the status information, and linking the new records to existing records.

One important process carried out by the server 20 is to correlate the Pharm ID with the information associated with the Internal ID to determine if there were any changes to the medication order transmitted by the pharmacy information system 35. If the correlation process in box 235 indicates that nothing has changed, meaning that the medication was actually dispensed to the patient as was directed in the medication order, then the server sends a record or message in box 240 to the eMAR system 45 containing information that is used by the eMAR system to update a patient's eMAR to reflect the treatment administered to the patient.

If the correlation process of box 235 carried out by the server indicates that a change has occurred, meaning that the medication was not delivered as prescribed in the original medication order, the server 20 issues a New Order ID and associates it with the information contained in the status message related to the delivery of the medication. After assigning the New Order ID in box 245, the server prepares a message containing data related to the delivery of the medication and transmits the message to the eMAR system 45 to update the patient's eMAR. In this way, a patient's eMAR contains all information related to the delivery of medication to the patient, and not just information related to the original medication order. This is particularly advantageous in that the system thus captures any changes made during delivery of the medication, such as, for example, when a care giver finds it necessary or desirable to titrate the delivery of medication to a patient using an infusion pump.

An alternative embodiment of the present invention includes the additional process, illustrated by box 250 of FIG. 3, whereby either the server 20, of some other hospital system, reconciles the various entries in the eMAR system for a patient to capture the medication history of the patient. In this process, the server 20 or other hospital system processes and arranges the records of the eMAR such that reports can be generated, viewed and printed wherein a care giver inspecting the report can easily see not only the original medication order, but also, typically in time order, the sequence of any changes that were made to the original medication by a care giver.

The correlation process carried out by the server 20 in box 235 (FIG. 3) may be performed in various ways, and the present invention is not intended to be limited by any particular process. For example, the server may analyze the status message received from the medication administration device by comparing the infusion status messages against the patient orders. If the status message fits another order better than the one it is reported against, the message will be flagged and the New Order ID assigned. This comparison may be done simply by matching data fields and detecting when a field differs from the original order, or it may be done using more sophisticated approaches, such as using a pattern matching algorithm, which may also include fuzzy logic, to determine which orders an infusion message best fits. One advantage of using a pattern matching algorithm is that status messages would not be required to exactly match an original order in length or content, and yet the server would still be able to analyze the message and match it up to an existing order.

Occasionally, a medication will be administered without any written order. Such an event may occur, for example, in the emergency room or may result from a verbal order given by an anesthesiologist during surgery. In such a case, the infusion bag is hung, the appropriate operating commands or parameters are entered into the infusion pump, and the administration is initiated by the care giver to deliver the medication to the patient. In such a case the process begins at box 215 of FIG. 3. The ensuing process, however, is very similar to that described above, the only difference being that there is no Pharm ID, since the medication delivery did not originate in the pharmacy system 45.

As previously described, initiation of medication administration in box 215 results in the medication administration device, here an infusion pump, assigning an Internal Order ID in box 220. When the server receives a status message transmitted by the infusion pump in box 225, the server attempts to correlate the Internal ID with a Pharm ID in box 230. Because there is no Pharm ID, the correlation analysis carried out in box 230 necessarily results in the program branching in box 235 to box 245, where the server issues a New Order ID. This New Order ID is then transmitted to the eMAR system 45 to update the patient's eMAR in box 240. In this manner, the system of the present invention automatically accounts for all medication administrations given to a patient, and ensures that the patient's eMAR accurately reflects the care that the patient received. The system of the present invention accomplishes this automatically, thus reducing the amount of manual record keeping and reconciliation that would otherwise be performed by a care giver or other staff member of the hospital or institution. Moreover, elimination of manual steps reduces the possibility of errors in transcribing and reconciling the information input into the patient's eMAR.

While several particular forms of the invention have been illustrated and described, it will be apparent that various modifications can be made without departing from the spirit and scope of the invention.

I claim:
1. A method comprising:
receiving, at a processor, medication administration parameters entered into a medication administration delivery device remote from the processor, the medication administration parameters being associated with a delivery of a medication to a patient by the medication administration delivery device, the medication being associated with a first order identification number;
electronically preventing, by the processor, without user interaction, the medication administration delivery device from delivering the medication responsive to determining, by the processor, that the medication administration parameters do not satisfy predetermined criteria for delivery of the medication to the patient;
automatically programming, by processor responsive to the medication administration parameters satisfying the predetermined criteria, the medication administration device to deliver the medication associated with the first order identification number, the programming comprising providing operating parameters of the medication administration delivery device;

receiving, over a network, an indication that the medication administration device initiated delivery of the medication according to the provided operating parameters;

receiving, at the processor from the medication administration device and without user interaction, medication administration status information comprising the first order identification number;

detecting, with the processor, from the received medication administration status information, a medication delivery change action indicating a change in the delivery of the medication for the first order identification number;

determining, with the processor, responsive to the detected medication delivery change action and without user interaction, to assign a second order identification number to the delivery of the medication based on information provided with the detected medication delivery change action; and updating, responsive to determining to assign the second order identification number, a medication administration record for a patient associated with the delivered medication, the medication administration record being updated with the second order identification number.

2. The method of claim 1, further comprising:
comparing information regarding actual delivery of the medication to medication delivery instructions of a medication order to detect the medication delivery change action.

3. The method of claim 1, further comprising receiving a medication order by a medication order source, wherein the operating parameters are based on the medication order.

4. The method of claim 3, wherein the medication order is stored in a medication administration record database.

5. The method of claim 1, wherein the operating parameters comprise instructions regarding how to deliver a medication corresponding to a medication order.

6. The method of claim 1, further comprising:
associating the second order identification number with the first order identification number.

7. The method of claim 1, further comprising:
transmitting, if the second order identification number is assigned, the second order identification number and information regarding the detected medication delivery change action.

8. The method of claim 1, further comprising:
transmitting, if the second order identification number is not assigned, the first order identification number and information regarding the detected medication delivery change action.

9. A system comprising:
a processor; and
a memory including executable instructions that, when executed by the processor, cause the processor to:
receive medication administration parameters entered into a medication administration device remote from the processor, the medication administration parameters being associated with a delivery of a medication to a patient by the medication administration device, the medication being associated with a first order identification number;
electronically prevent without user interaction, the medication administration device from delivering the medication responsive to determining that the medication administration parameters do not satisfy predetermined criteria for delivery of the medication to the patient;
automatically program, responsive to the medication administration parameters satisfying the predetermined criteria, the medication administration to deliver the medication associated with the first order identification number, including providing operating parameters of the medication administration device;
receive an indication that the medication administration device initiated delivery of the medication according to the provided operating parameters;
receive medication administration status information from the medication administration device, the medication administration status information comprising the first order identification number;
detect, from the received medication administration status information, a medication delivery change action indicating a change in the delivery of the medication for the first order identification number;
determine, based on the detected medication delivery status information, to assign a second order identification number to the delivery of the medication based on information provided with the detected medication delivery change action, and
update, responsive to determining to assign the second order identification number, a medication administration record for a patient associated with the delivered medication, the medication administration record being updated with the second order identification number.

10. The system of claim 9, wherein the medication administration device is further configured to:
compare information regarding actual delivery of the medication to medication delivery instructions of a medication order to detect the medication delivery change action.

11. The system of claim 9, wherein the operating parameters comprise instructions regarding how to deliver a medication corresponding to a medication order.

12. The system of claim 9, wherein the executable instructions that, when executed by the processor, cause the processor to:
associate the second order identification number with the first order identification number.

13. The system of claim 9, wherein the executable instructions that, when executed by the processor, cause the processor to:
transmit, if the second order identification number is assigned, the second order identification number and information regarding the detected medication delivery change action.

14. The system of claim 9, the executable instructions that, when executed by the processor, cause the processor to:
transmit, if a second order identification number is not assigned, the first order identification number and information regarding the detected medication delivery change action.

15. A non-transitory machine-readable medium comprising instructions stored therein, which when executed by a machine, cause the machine to perform operations, the non-transitory machine-readable medium comprising:
receiving, at a processor, medication administration parameters entered into a medication administration device remote from the processor, the medication administration parameters being associated with a delivery of a medication to a patient by the medication administration device, the medication being associated with a first order identification number;

electronically preventing, by the processor, without user interaction, the medication administration device from delivering the medication when the medication administration parameters do not satisfy predetermined criteria for delivery of the medication to the patient;
instructions for automatically programming, when the medication administration parameters satisfy the predetermined criteria, the medication administration device remote from the machine to deliver the medication associated with a first order identification number, the programming comprising providing operating parameters of the medication administration device;
instructions for receiving an indication that the medication administration device initiated delivery of the medication according to the provided operating parameters;
instructions for receiving, from the medication administration device, medication administration status information, the medication administration status information comprising the first order identification number;
instructions for detecting, from the received medication administration status information, a medication delivery change action indicating a change in the delivery of the medication for the first order identification number;
instructions for determining, responsive to the detected medication delivery change action, to assign a second order identification number to the delivery of the medication based on information provided with the detected medication delivery change action; and
instructions for updating, responsive to determining to assign the second order identification number, a medication administration record for a patient associated with the delivered medication, the medication administration record being updated with the second order identification number.

16. The non-transitory machine-readable medium of claim 15, wherein the operating parameters comprise instructions regarding how to deliver a medication corresponding to a medication order.

17. The non-transitory machine-readable medium of claim 15, further comprising:
instructions for associating the second order identification number with the first order identification number.

18. The non-transitory machine-readable medium of claim 15, further comprising:
instructions for transmitting, if the second order identification number is assigned, the second order identification number and information regarding actual delivery of the medication.

19. The non-transitory machine-readable medium of claim 15, further comprising:
instructions for transmitting, if the second order identification number is not assigned, the first order identification number and information regarding the detected medication delivery change action.

20. The method of claim 1, wherein receiving the medication administration status information from the medication administration device comprises periodically receiving status messages containing information related to the delivery of the medication.

* * * * *